United States Patent [19]

Yokohama et al.

[11] Patent Number: 5,306,845

[45] Date of Patent: Apr. 26, 1994

[54] METHOD FOR PRODUCING AN ALDEHYDE

[75] Inventors: Toshiharu Yokohama; Naoko Fujita, both of Yokohama; Takao Maki, Fujisawa, all of Japan

[73] Assignee: Mitsubishi Kasei Corporation, Tokyo, Japan

[21] Appl. No.: 82,366

[22] Filed: Jun. 28, 1993

[51] Int. Cl.$^5$ .............................................. C07C 45/41
[52] U.S. Cl. .................................. 568/484; 568/426; 568/435; 568/449
[58] Field of Search ................ 568/449, 484, 426, 435

[56] References Cited

U.S. PATENT DOCUMENTS 3,884,981  5/1975  Kiff ...................................... 568/484
4,093,661  6/1978  Trecker et al. ...................... 568/435
4,613,700  8/1986  Maki et al. .......................... 568/435
5,059,711  10/1991 Joentgen et al. .................... 568/435

*Primary Examiner*—Werren B. Lone
*Attorney, Agent, or Firm*—Oblon, Spivak, McClelland, Maier & Neustadt

[57] ABSTRACT

A method for producing an aldehyde, which comprises hydrogenating a carboxylic acid or its alkyl ester with molecular hydrogen in the presence of a catalyst, wherein (1) chromium oxide of high purity having a specific surface area of at least 10 $m^2/g$ and a total content of sodium, potassium, magnesium and calcium of not more than 0.4 wt %, is used as the catalyst, and (2) the hydrogenation reaction is conducted while maintaining the carboxylic acid or its alkyl ester at a concentration of not more than 10 vol %.

13 Claims, No Drawings

METHOD FOR PRODUCING AN ALDEHYDE

BACKGROUND OF THE INVENTION

1. Field of the Invention

The present invention relates to a method for producing an aldehyde useful as e.g. an intermediate for organic syntheses. More particularly, it relates to a method for producing an aldehyde by a hydrogenation reaction of a carboxylic acid or its alkyl ester.

2. Discussion of Background

Heretofore, various methods have been reported for the production of aldehydes. As the most commonly employed method using a carboxylic acid or its derivative as the starting material, so-called Rosenmund reduction method via a carboxylic acid chloride may be mentioned. However, this method has a drawback that the production costs are high.

It is most preferred if it is possible to efficiently produce an aldehyde by reducing a carboxylic acid directly with molecular hydrogen. However, such a method has been believed to be extremely difficult. Namely, with respect to the hydrogenation reaction of a carboxylic acid or its derivative, a method of using yttrium oxide as the catalyst (see U.S. Pat. No. 4,328,373) or a method of using aluminum oxide (see U.S. Pat. No. 3,935,265) has, for example, been reported. However, these methods have a problem with respect to the catalytical activity and selectivity for the aldehyde.

It has been reported that when a cycloalkyl ester of a lower fatty acid such as acetic acid or n-butyric acid is hydrogenated by using complex oxide of zinc and chromium as a catalyst, the corresponding acetaldehyde or n-butyl aldehyde was formed although in poor yield (see Japanese Examined Patent Publication No. 38410/1972), and it has been reported also that when methyl benzoate, pivalic acid or the like is hydrogenated by using iron oxide containing a small amount of chromium oxide, as a catalyst, the corresponding aldehyde will be formed in a yield of certain degree (see European Patent No. 304853). With these catalysts, it is difficult to attain practically satisfactory yield of aldehydes, although the hydrogenation reaction proceeds to some extent.

The present inventors have previously reported on a method for producing an aldehyde by a hydrogenation reaction of the corresponding carboxylic acid or its ester by means of a catalyst composed essentially of zirconium oxide and slight amount of chromium e.t.c. (see U.S. Pat. No. 4,613,700 and Japanese Unexamined Patent Publications No. 152434/1985 and No. 115043/1986).

By this method, when an aliphatic carboxylic acid having two hydrogen atoms bonded to the carbon at the α-position to the carboxyl group, or its ester, was used as the starting material, a ketone product was produced as a byproduct by decarboxylation condensation, whereby the selectivity for the desired aldehyde was not necessarily adequate. Also in the case where a heterocyclic carboxylic acid containing a hetero atom such as N, S or O in the heterocyclic ring, or its ester, was used as the starting material, the selectivity for the aldehyde was also inadequate. Thus, it has been desired to develop a catalyst with a higher performance suitable for commercial purpose.

As described above, according to the reports available heretofore, a method for efficiently producing aldehydes by directly hydrogenating various carboxylic acids of aliphatic, alicyclic, aromatic or heterocyclic type, or their derivatives, has not yet been established, and there are many problems to be solved, such as improvement of the catalytic activities and the selectivity for the desired products, and prolongation of the effective life of the catalysts.

SUMMARY OF THE INVENTION

It is an object of the present invention to solve the above-mentioned problems of the conventional methods and to provide a method for producing aldehydes at high selectivity directly from various carboxylic acids of e.g. aliphatic, alicyclic, aromatic or heterocyclic type, or their alkyl esters.

The present invention provides a method for producing an aldehyde, which comprises hydrogenating a carboxylic acid or its alkyl ester with molecular hydrogen in the presence of a catalyst, wherein (1) chromium oxide of high purity having a specific surface area of at least 10 m$^2$/g and a total content of sodium, potassium, magnesium and calcium of not more than 0.4 wt %, is used as the catalyst, and (2) the hydrogenation reaction is conducted while maintaining the carboxylic acid or its alkyl ester at a concentration of not more than 10 vol %.

According to the study by the present inventors, when an aldehyde was produced by hydrogenating a carboxylic acid by using a commonly available chromium oxide, the catalytic activities or selectivity for the desired aldehyde was poor, and it was impossible to obtain satisfactory results.

Under these circumstances, the present inventors have conducted extensive studies on chromium oxide, particularly with respect to the impurities contained, the relation with the physical properties of the catalyst, and the reaction conditions, whereupon it has been found that good results are obtainable only when the reaction is conducted by using a specific chromium oxide having a large specific surface area and a total content of impurities such as sodium, potassium, magnesium and calcium being not higher than a specified level, while maintaining the carboxylic acid or its alkyl ester at a concentration of not higher than a certain specified level in a reaction phase. The present invention has been accomplished on the basis of this discovery.

DETAILED DESCRIPTION OF THE PREFERRED EMBODIMENTS

Now, the present invention will be described in detail.

The starting material of the present invention is an aliphatic, alicyclic, aromatic or heterocyclic carboxylic acid or its alkyl ester.

The aliphatic carboxylic acid may, for example, be a C$_{2-24}$ saturated or unsaturated carboxylic acid such as acetic acid, propionic acid, butyric acid, isobutyric acid, pivalic acid, valeric acid, hexanoic acid, heptanoic acid, ocatanoic acid, 2-ethylhexanoic acid, nonanoic acid, decanoic acid, undecanoic acid, lauric acid, tridecanoic acid, tetradecanoic acid, pentadecanoic acid, hexadecanoic acid, stearic acid, isostearic acid, nonadecanoic acid, tricosanoic acid, tetracosanoic acid, 10-undecenoic acid, oleic acid or 11-eicosenoic acid. Further, a polycarboxylic acid such as oxalic acid, malonic acid, diethylmalonic acid, succinic acid, glutaric acid, adipic acid, decanedioic acid or octadecanedioic acid, may also be used.

The alicyclic carboxylic acid may, for example, be a $C_{5-6}$ saturated cycloalkane mono- or polycarboxylic acid such as a cyclopentanecarboxylic acid, cyclohexane-carboxylic acid or 1,4-cyclohexanedicarboxylic acid.

Further, the aliphatic carboxylic acid or the alicyclic carboxylic acid may have a group inert to the reaction as a substituent. Such a substituent may, for example, be an aryl group, a heterocyclic group containing a hetero atom such as O, S or N, or an alkoxy group.

The aromatic carboxylic acid or its alkyl ester to be used in the present invention may be represented by the formula $Ar-(COOR)_n$ wherein n is 1 or 2, R is a hydrogen atom or an alkyl group, and Ar is an aryl group which may have a substituent.

The aryl group may, usually, be a phenyl group, a naphthyl group or an anthryl group. The substituent on the aryl group is a group inert to the reaction, and it may, for example, be an alkyl group, a cycloalkyl group, an alkoxy group, an aryloxy group, a halogen atom, a hydroxyl group, a formyl group or an acyl group. Further, when n=2, two R may be the same or different. As a specific compound, a carboxylic acid such as benzoic acid, toluic acid, dimethylbenzoic acid, cyclohexylbenzoic acid, cuminic acid, t-butylbenzoic acid, phenylbenzoic acid, anisic acid, phenoxybenzoic acid, chlorobenzoic acid, hydroxybenzoic acid, acetylbenzoic acid, naphthoic acid or anthracene carboxylic acid, may be mentioned. Further, phthalic acid and its dialkyl ester may also be used.

The heterocyclic carboxylic acid or its alkyl ester to be used as the starting material in the present invention may, for example, be a carboxylic acid of a 5-or 6-member heterocyclic ring containing at least one N, S or O atom, such as a pyrrole ring, a furan ring, a thiophene ring, an oxazole ring, a thiazole ring, an oxazoline ring, an imidazole ring, an imidazoline ring, a pyrazole, a pyran ring, a thiopyran ring, a pyridine ring, a quinoline ring, an oxazine ring, a thiazine ring, a pyrimidine ring, a pyrazine ring, a triazine ring, an azepine ring or an oxepine ring, a carboxylic acid of a condensed ring having at least two such 5- or 6-member heterocyclic rings condensed, or a carboxylic acid of a condensed ring having such a 5- or 6-member heterocyclic ring and an aromatic ring such as a benzene ring condensed, or an alkyl ester thereof. They may have a substituent inert to the reaction. Specifically, nicotinic acid, furan carboxylic acid and thiazole carboxylic acid as well as alkyl esters thereof such as methyl, ethyl and n-butyl esters thereof, may be mentioned.

As such a carboxylic acid or its alkyl ester, a $C_{1-4}$ linear or branched alkyl ester such as methyl ester, ethyl ester, n-butyl ester or isobutyl ester, is most preferred.

Among these carboxylic acids or their alkyl esters as starting materials, particularly preferred in the present present invention are saturated and unsaturated aliphatic carboxylic acids having at least 5 carbon atoms or their alkyl esters, and alicyclic carboxylic acids or their alkyl esters.

As the catalyst to be used in the present invention, chromium oxide having a total content of sodium, potassium, magnesium and calcium of not more than 0.4 wt %, is used.

If chromium oxide contains these impurities such as sodium, potassium, magnesium and calcium beyond the specified concentration, there will be not only a substantial deterioration in the catalytic activities and in the selectivity for the aldehyde, but also adverse effects against the useful life of the catalyst and against the stability of the catalyst.

Further, the specific surface area of chromium oxide in the present invention must be at least 10 $m^2/g$, preferably from 10 to 200 $m^2/g$. If the specific surface area is less than 10 $m^2/g$, there will be a deterioration in the catalytic activities even if the total content of sodium, potassium, magnesium and calcium satisfies the condition of not more than 0.4 wt %.

It is convenient if it is possible to use commercially available chromium oxide as the material for the chromium oxide catalyst to be used in the present invention. However, widely distributed commercial products can not be used by themselves even when the total content of Na, K, Mg and Ca is less than the specified concentration, because the specific surface area is less than 10 $m^2/g$ since they are calcined at a high temperature.

As the starting material for the catalyst, hydroxide, sulfate, nitrate or halide of chromium, or chromic anhydride or dichromic acid, or its inorganic salt such as ammonium salt or an alkali metal salt, or an organic salt such as formate, acetate, oxalate or organic metal complex of chromium, can be used. However, most of commercially available starting materials contain Na, K, Mg and Ca in a total amount of more than 0.4 wt %. Therefore, when such starting materials are used, it is necessary to remove Na, K, Mg and Ca by a method which will be described hereinafter so that the total content of such impurities will be not more than the specified concentration.

Further, in some cases, even a commercially available chromium hydroxide material may be of high purity so that the total content of sodium, potassium, magnesium and calcium is not more than 0.4 wt %. Therefore, if such a material is selected, it may be used by itself as the starting material.

Chromium oxide to be used in the present invention, can be prepared by directly decomposing the above-mentioned starting material compound or by converting it to a hydroxide, followed by drying and calcining. However, a due care must be taken when a compound containing Na, K, Mg and Ca elements is used for the process for the preparation. For example, in a case where chromium sulfate, nitrate or halide is used as the starting material, and it is precipitated by an alkali metal hydroxide such as sodium hydroxide or potassium hydroxide in the form of chromium hydroxide to use as the starting material for the chromium oxide catalyst of the present invention. If washing of the staring material is inadequate, sodium or potassium will remain in the resulting catalyst, whereby a highly active catalyst can not be obtained. Accordingly, in such a case, it is necessary to thoroughly wash the resulting catalyst to remove such elements to a level of not more than the specified concentration.

It is preferred that instead of such an alkali metal hydroxide, aqueous ammonia is used to convert the starting material to a hydroxide, followed by washing with water, drying and calcining, whereby it is possible to obtain a chromium oxide catalyst having a low content of alkali metal elements such as sodium and potassium.

Further, in a case where chromium sulfate, nitrate or halide is used as the starting material, and it is precipitated in the form of chromium hydroxide, which is then used as the starting material for the chromium oxide catalyst of the present invention, if the starting material contains a magnesium salt or a calcium salt, such a salt will react with sodium hydroxide, potassium hydroxide or aqueous ammonia to form magnesium or calcium hydroxide which is insoluble in water, and such a component can not be removed even if washing is thoroughly conducted, whereby a highly active catalyst can not be obtained. Therefore, the starting material to be used should not contain a magnesium salt and a calcium salt as impurities in an amount exceeding the specified level.

In general, a chromium hydroxide is precipitated with an aqueous ammonia from a chromium salt as a starting material.

However, said chromium salt contains a magnesium salt and a calcium salt as impurities. If aqueous ammonia where the hydroxyl ion concentration is not so high, is used, precipitation of magnesium hydroxide or calcium hydroxide derived from magnesium salt and calcium salt containing in the chromium salt, tends to be incomplete, whereby it is possible to obtain chromium hydroxide having a lower content of such impurities. It is because the solubility product of magnesium hydroxide $[[Mg^{2+}][OH^-]^2 = 1.8 \times 10^{-11}]$ or the solubility product of calcium hydroxide $[[Ca^{2+}][OH^-]^2 = 5.5 \times 10^{-6}]$ is sufficiently larger than the solubility product of chromium hydroxide $[[Cr^{3+}][OH^-]^3 = 6 \times 10^{-31}]$. Further, in such a case, if ammonium salt such as chloride is added to hinder dissociation of aqueous ammonia and reduce the concentration of hydroxyl ions, precipitation of magnesium hydroxide or calcium hydroxide can be prevented, whereby it is possible to obtain chromium hydroxide having a less content of such impurities. By using such chromium hydroxide, it is possible to obtain a chromium oxide catalyst having a less content of impurities.

Otherwise, it is possible to obtain a chromium oxide catalyst to be used in the present invention also by calcining commercially available chromium hydroxide. However, most of chromium hydroxide usually contain a sodium, potassium, magnesium or calcium compound, whereby it is difficult to obtain a catalyst having adequate catalytic activities by simple calcination.

Accordingly, when commercially available chromium hydroxide containing such impurities, is used, it is necessary to conduct purification before calcining.

The temperature for calcining such a starting material for the chromium oxide catalyst is usually within a range of from 400° to 1,000° C., preferably from 500° to 1,000° C. When the calcining temperature is low, the specific surface area of the catalyst tends to be large, which is desirable from the viewpoint of the reactivity, but is not so desirable from the viewpoint of the useful life of the catalyst.

The chromium oxide catalyst to be used in the present invention, can be molded by a conventional method. For example, it is possible to employ a tabletting method, a method of spray drying, followed by calcining, or a method wherein water is added to a powder of chromium hydroxide or chromium oxide, followed by mixing, if necessary in the presence of a binder component, and the mixture is extrusion molded, followed by drying and calcining at a predetermined temperature. Further, the chromium oxide catalyst may be used as supported on a carrier inert to the main reaction.

The hydrogenation by molecular hydrogen in the present invention is advantageously carried out in a vapor phase. The reaction temperature is particularly suitably at a level of from 200° to 500° C., preferably from 250° to 450° C. Further, the reaction pressure may be atmospheric pressure or a slightly elevated state.

In the present invention, the hydrogenation reaction is preferably conducted with a fixed bed of the catalyst molded as described above. In such a case, the concentration of the carboxylic acid or its alkyl ester in the feed material is usually not higher than 10 vol %, preferably from 0.01 to 10 vol %, more preferably from 0.1 to 10 vol %, in the vapor phase. If this concentration is too low, the reaction efficiency tends to be poor. On the other hand, if the concentration is too high, there will be problems such that the conversion of the starting material and selectivity for the aldehyde tend to be poor, and the useful life of the catalyst will be shortened.

With respect to the space velocity of the feed material to bring the concentration in such a range, LHSV of the starting material carboxylic acid or its alkyl ester is usually from 0.01 to 2 hr$^{-1}$ (kg/l-catalyst-hr), preferably from 0.03 to 1 hr$^{-1}$.

Hydrogen is supplied in such an amount that within the above-mentioned LHSV range of the starting material, the concentration of the starting material will be not higher than 10 vol %, and the supply rate of hydrogen is usually from 300 to 20,000 hr$^{-1}$, preferably from 300 to 5,000 hr$^{-1}$ as GHSV.

The hydrogen to be used may contain some inert gas such as nitrogen, carbon dioxide or steam.

The present catalyst has especially remarkable advantage in the case of the hydrogenation of aliphatic unsaturated carboxylic acids.

When a hitherto known catalyst of the type having slight amount of chromium incorporated to zirconium oxide, was used, or when a chromium oxide catalyst having a concentration of impurities higher than that of the present invention, was used, there were problems such that the yield of the desired aldehyde was poor, because aldehyde produced by hydrogenation and non-reacted acid was isomerized, whereby the position of the double bond changed.

Whereas, by the method of the present invention using such a specific catalyst, the desired aldehyde can be obtained at high selectivity without the positional change of the double bond.

In the present invention, a $C_{5-24}$ mono-unsaturated aliphatic carboxylic acid or its alkyl ester is preferably used as the starting material. Such a starting material carboxylic acid may, for example, be 10-undecenoic acid, 11-eicocenoic acid or oleic acid.

By the method of the present invention, an aldehyde can be produced at high selectivity by direct hydrogenation of a carboxylic acid or its alkyl ester under specific conditions using a specific catalyst. Therefore, the method of the present invention is industrially very important.

Now, the present invention will be described in further detail with reference to Examples and Comparative Examples. However, it should be understood that the present invention is by no means restricted to such specific Examples.

Preparation of Chromium Oxide Catalysts

The catalysts A to O used hereinafter were prepared from chromium oxide powder by tabletting and followed by sieving to a size of from 10 to 20 mesh.

Catalysts A to K:

Various commercially available chromium hydroxides as starting materials were used and calcined in air at 700° C. for 3 hours to obtain chromium oxide powders.

Catalyst L:

The same chromium hydroxide starting material as used for Catalyst A was used and calcined in air at 500° C. for 3 hours to obtain a chromium oxide powder.

Catalyst M:

The same chromium hydroxide starting material as used for Catalyst A was used and calcined in air at 1,060° C. for 3 hours to obtain a chromium oxide powder.

Catalysts G, H, I and J had a specific surface area of at least 10 m$^2$/g, but contained more than 0.4 wt % in a total amount of sodium, potassium, magnesium and calcium.

Catalyst K had a total content of sodium, potassium, magnesium and calcium of not higher than 0.4 wt %, but contained 0.5 wt % of silicon. Further, the specific surface area was at least 10 m$^2$/g.

Catalysts M and O had a total content of sodium, potassium, magnesium and calcium of not more than 0.4 wt %, but the specific surface area was lower than 10 m$^2$/g.

TABLE 1

Contents (wt %) of impurities in chromium oxide catalysts and specific surface area (m$^2$/g) of the catalyst

| Chromium oxide catalyst | Starting material for chromium oxide | Calcining temp. (°C.) | Impurities in chromium oxide (wt %) | | | | | Specific surface area (BET method) (m$^2$/g) | Notes |
|---|---|---|---|---|---|---|---|---|---|
| | | | Na | K | Mg | Ca | Na + K + Mg + Ca | | |
| A | Chromium hydroxide | 700 | ND | ND | ND | 0.05 | 0.05 | 15.1 | |
| B | Chromium hydroxide | 700 | 0.11 | ND | ND | 0.05 | 0.16 | ≧10 | |
| C | Chromium hydroxide | 700 | ND | ND | ND | 0.13 | 0.13 | ≧10 | |
| D | Chromium hydroxide | 700 | 0.20 | ND | ND | 0.04 | 0.24 | ≧10 | |
| E | Chromium hydroxide | 700 | 0.11 | ND | ND | 0.15 | 0.26 | ≧10 | |
| F | Chromium hydroxide | 700 | 0.19 | ND | ND | 0.16 | 0.35 | ≧10 | |
| G | Chromium hydroxide | 700 | 0.21 | ND | ND | 0.25 | 0.46 | ≧10 | |
| H | Chromium hydroxide | 700 | 0.39 | ND | ND | 0.22 | 0.61 | ≧10 | |
| I | Chromium hydroxide | 700 | ND | 0.68 | 0.42 | 0.05 | 1.15 | ≧10 | |
| J | Chromium hydroxide | 700 | 0.70 | ND | 0.06 | 0.60 | 1.36 | 17.7 | |
| K | Chromium hydroxide | 700 | ND | ND | ND | 0.05 | 0.05 | ≧10 | 0.5 wt % of Si |
| L | Same material as for catalyst A | 500 | ND | ND | ND | 0.05 | 0.05 | 26.5 | |
| M | Same material as for catalyst A | 1060 | ND | ND | ND | 0.05 | 0.05 | 6.4 | |
| N | Precipitation method | 700 | ND | ND | ND | ND | — | 15.4 | |
| O | Chromium oxide of reagent grade | — | ND | ND | ND | 0.03 | 0.03 | 3.0 | |

Catalyst N:

To an aqueous solution comprising 151.9 g of chromium nitrate nonahydrate and 500 ml of water, 6N aqueous ammonia was added dropwise under stirring for controlling the pH to 8.0. The obtained hydroxide was collected by filtration, washed with water and dried, and then it was calcined in air at 700° C. for 3 hours to obtain a chromium oxide powder.

Catalyst O

Commercially available chromium oxide powder of reagent grade was used as supplied.

The contents of sodium, potassium, magnesium and calcium contained in these chromium oxide catalysts A to O prepared by the above methods and the specific surface areas measured by a BET method are shown in Table 1.

Catalysts A to F, L and N had a total content of sodium, potassium, magnesium and calcium of not more than 0.4 wt %, and a specific surface area of at least 10 m$^2$/g.

EXAMPLE 1

Using chromium oxide catalyst A, the hydrogenation reaction of stearic acid was conducted under atmospheric pressure at a reaction temperature of 350° C. under such conditions that the space velocity of stearic acid: LHSV =0.23 hr$^{-1}$ (kg/l-catalyst-hr), the space velocity of hydrogen: GHSV=1250 hr$^{-1}$ (concentration of starting material: 1.4 vol %).

The conversion of the stearic acid was 92.9%, and selectivity for stearyl aldehyde was 90.0%, as shown in Table 2.

EXAMPLES 2 to 6

The hydrogenation reaction of stearic acid was conducted in the same manner as in Example 1 except that chromium oxide catalysts B, C, D, E and F were used. The results are shown in Table 2.

EXAMPLE 7

The hydrogenation reaction of stearic acid was conducted in the same manner as in Example 1 except that chromium oxide catalyst K was used. Chromium oxide catalyst K had a total content of sodium, potassium, magnesium and calcium of not more than 0.4 wt %, but it contained 0.5 wt % of silicon as an additional impurity.

The conversion of stearic acid was 88.2%, and selectivity for stearyl aldehyde was 90.8%, as shown in Table 2.

COMPARATIVE EXAMPLES 1 to 4

The hydrogenation reaction of stearic acid was conducted in the same manner as in Example 1 except that chromium oxide catalysts G, H, I and J were used. The results are shown in Table 2.

EXAMPLE 8

The hydrogenation reaction of stearic acid was conducted in the same manner as in Example 1 except that chromium oxide catalyst L was used. The results are shown in Table 2.

COMPARATIVE EXAMPLES 5 to 6

The hydrogenation reaction of stearic acid was conducted in the same manner as in Example 1 except that chromium oxide catalysts M and O were used. The results are shown in Table 2.

TABLE 2

| | Results of hydrogenation reaction of stearic acid | | |
|---|---|---|---|
| | Chromium oxide catalyst | Conversion of stearic acid (%) | Selectivity for stearyl aldehyde (%) |
| Example 1 | A | 92.9 | 90.0 |
| Example 2 | B | 85.2 | 91.0 |
| Example 3 | C | 94.7 | 87.1 |
| Example 4 | D | 82.3 | 86.4 |
| Example 5 | E | 82.6 | 88.0 |
| Example 6 | F | 82.9 | 87.9 |
| Example 7 | K | 88.2 | 90.8 |
| Comparative Example 1 | G | 82.2 | 63.2 |
| Comparative Example 2 | H | 58.4 | 68.3 |
| Comparative Example 3 | I | 68.1 | 63.7 |
| Comparative Example 4 | J | 47.4 | 57.1 |
| Example 8 | L | 88.2 | 90.8 |
| Comparative Example 5 | M | 67.6 | 87.1 |
| Comparative Example 6 | O | 61.5 | 83.8 |

EXAMPLE 9

Using chromium oxide catalyst A, the hydrogenation reaction of stearic acid was conducted under atmospheric pressure at a reaction temperature of 320° C. under such conditions that the space velocity of stearic acid: LHSV =0.11 kg/l-catalyst-hr, and the space velocity of hydrogen: GHSV=1260 hr$^{-1}$ (concentration of starting material: 0.7 vol %).

The conversion of stearic acid was 86.3%, and selectivity for stearyl aldehyde was 91.3%.

EXAMPLE 10

Using chromium oxide catalyst A, the hydrogenation reaction of stearic acid was conducted under atmospheric pressure at a reaction temperature of 350° C. under such conditions that the space velocity of stearic acid: LHSV =0.23 kg/l-catalyst-hr, and the space velocity of hydrogen: GHSV=435 hr$^{-1}$ (concentration of starting material: 4.0 vol %).

The conversion of stearic acid was 91.7%, and selectivity for stearyl aldehyde was 88.6%.

COMPARATIVE EXAMPLE 7

Using chromium oxide catalyst A, the hydrogenation reaction of stearic acid was conducted under atmospheric pressure at a reaction temperature of 350° C. under such conditions that the space velocity of stearic acid: LHSV =0.23 kg/l-catalyst-hr, and the space velocity of hydrogen: GHSV=163 hr$^{-1}$ (concentration of starting material: 10.2 vol %).

The conversion of stearic acid was 78.2%, and selectivity for stearyl aldehyde was 52.3%.

EXAMPLE 11

Using chromium oxide catalyst N, the hydrogenation reaction of stearic acid was conducted under atmospheric pressure at a reaction temperature of 330° C. under such conditions that the space velocity of stearic acid: LHSV =0.11 kg/l-catalyst-hr, and the space velocity of hydrogen: GHSV=1250 hr$^{-1}$ (concentration of starting material: 1.4 vol %).

The conversion of stearic acid was 84.7%, and selectivity for stearyl aldehyde was 95.1%.

COMPARATIVE EXAMPLE 8

To 23.4 g of commercially available zirconyl hydroxide ($ZrO_2$ content: 85.4 wt %), an aqueous solution comprising 3.25 g of chromium nitrate nonahydrate and 50 ml of water, was added and evaporated to dryness, and the dried product was calcined in air at 700° C. for 3 hours to obtain an oxide comprising chromium and zirconium (chromium:zirconium=5:100 atomic ratio). The catalyst was prepared by tabletting the obtained powder, and followed by sieving to a size of from 10 to 20 mesh.

This catalyst had a total content of sodium, potassium, magnesium and calcium of not more than 200 ppm and a specific surface area of 72.0 m$^2$/g.

Using the above catalyst, the hydrogenation reaction of stearic acid was conducted in the same manner as in Example 1. The conversion of stearic acid was 93.6%, but selectivity for stearyl aldehyde was as low as 45.4%.

COMPARATIVE EXAMPLE 9

A powder of zinc oxide-chromium oxide (30:70 wt %) was co-precipitated from a zinc nitrate-chromium nitrate aqueous solution by aqueous ammonia and then calcined in air at 700° C. for 3 hours. Using this powder, tabletting was conducted, followed by sieving to a size of from 10 to 20 mesh to obtain a zinc oxide-chromium oxide catalyst.

This catalyst had a total content of sodium, potassium, magnesium and calcium of not more than 200 ppm and a specific surface area of 27.3 m$^2$/g.

Using the above catalyst, the hydrogenation reaction of stearic acid was conducted under the same conditions as in Example 1.

The conversion of stearic acid was 92.6%, but selectivity for stearyl aldehyde was as low as 62.7%.

EXAMPLE 12

Using chromium oxide catalyst A, the hydrogenation reaction of 10-undecenoic acid was conducted under atmospheric pressure at a reaction temperature of 370° C. under such conditions that the space velocity of 10-undecenoic acid: LHSV=0.11-kg/l-catalyst-hr, and the space velocity of hydrogen: GHSV=1250 hr$^{-1}$ (concentration of starting material: 1.1 vol %).

The conversion of 10-undecenoic acid was 86.6%, selectivity for undecenyl aldehyde was 97.2%, and selectivity for 10-undecenyl aldehyde was 92.0%.

COMPARATIVE EXAMPLE 10

The hydrogenation reaction of 10-undecenoic acid was conducted in the same manner as in Example 12 except that chromium oxide catalyst J was used.

The conversion of 10-undecenoic acid was 32.0%, and selectivity for undecenyl aldehyde was 42.9%.

COMPARATIVE EXAMPLE 11

The hydrogenation reaction of 10-undecenoic acid was conducted in the same manner as in Example 12 except that an oxide catalyst comprising chromium and zirconium of Comparative Example 8 was used. The reaction was conducted at a temperature of 340° C., whereby the conversion of 10-undecenoic acid was 69.6%, selectivity for undecenyl aldehyde was 79.4%, and selectivity for 10-undecenyl aldehyde was 43.7%.

EXAMPLE 13

Using chromium oxide catalyst A, the hydrogenation reaction of n-caprylic acid was conducted under atmospheric pressure at a reaction temperature of 360° C. under such conditions that the space velocity of n-caprylic acid: LHSV=0.11 kg/l-catalyst-hr, and the space velocity of hydrogen: GHSV=1250 hr$^{-1}$ (concentration of starting material: 1.4 vol %).

Upon expiration of 5 hours after the initiation of the reaction, the conversion of caprylic acid was 97.2%, and selectivity for capryl aldehyde was 97.0%. With respect to the results of the reaction upon expiration of 25 hours, the conversion of caprylic acid was 96.0%, and selectivity for capryl aldehyde was 97.5%. Thus, no deterioration in the catalytic activities was observed.

COMPARATIVE EXAMPLE 11

Using chromium oxide catalyst A, the hydrogenation reaction of n-caprylic acid was conducted under atmospheric pressure at a reaction temperature of 440° C. under such conditions that the space velocity of n-caprylic acid: LHSV=0.73 kg/l-catalyst-hr, and the space velocity of hydrogen: GHSV=640 hr$^{-1}$ (concentration of starting material: 15.0 vol %).

Upon expiration of 6 hours after the initiation of reaction, the conversion of caprylic acid was 84.0%, and selectivity for capryl aldehyde was 93.0%. With respect to the results of the reaction upon expiration of 25 hours, the conversion of caprylic acid was 78.0%, and selectivity for capryl aldehyde was 92.1%. Thus, a deterioration in the yield of aldehyde was observed.

EXAMPLE 14

Using chromium oxide catalyst N, the hydrogenation reaction of lauric acid was conducted under atmospheric pressure at a reaction temperature of 360° C. under such conditions that the space velocity of lauric acid: LHSV =0.11 kg/l-catalyst-hr, and the space velocity of hydrogen: GHSV=1250 hr$^{-1}$ (concentration of starting material: 1.4 vol %).

The conversion of lauric acid was 92.0%, and selectivity for lauryl aldehyde was 93.1%.

EXAMPLE 15

Using chromium oxide catalyst A, the hydrogenation reaction of cyclohexane carboxylic acid was conducted under atmospheric pressure at a reaction temperature of 370° C. under such conditions that the space velocity of cyclohexane carboxylic acid: LHSV=0.11 kg/l-catalyst-hr, and the space velocity of hydrogen: GHSV=1250 hr$^{-1}$ (concentration of starting material: 1.4 vol %).

The conversion of cyclohexane carboxylic acid was 92.2%, and selectivity for cyclohexane carboaldehyde was 96.9%.

EXAMPLE 16

Using chromium oxide catalyst A, the hydrogenation reaction of benzoic acid was conducted under atmospheric pressure at a reaction temperature of 390° C. under such conditions that the space velocity of benzoic acid: LHSV =0.13 kg/l-catalyst-hr, and the space velocity of hydrogen: GHSV=1250 hr$^{-1}$ (concentration of starting material: 1.9 vol %).

The conversion of benzoic acid was 89.7%, and selectivity for benzaldehyde was 98.9%.

What is claimed is:

1. A method for producing an aldehyde, which comprises hydrogenating a carboxylic acid or its alkyl ester with molecular hydrogen in the presence of a catalyst, wherein (1) chromium oxide of high purity having a specific surface area of at least 10 m$^2$/g and a total content of sodium, potassium, magnesium and calcium of not more than 0.4 wt %, is used as the catalyst, and (2) the hydrogenation reaction is conducted while maintaining the carboxylic acid or its alkyl ester at a concentration of not more than 10 vol %.

2. The method according to claim 1, wherein the carboxylic acid or its alkyl ester is an aliphatic, alicyclic, aromatic or heterocyclic carboxylic acid or its alkyl ester.

3. The method according to claim 1, wherein the carboxylic acid or its alkyl ester is a $C_{2-24}$ saturated or unsaturated mono- or poly-aliphatic carboxylic acid which may have a substituent inert to the reaction, or ts alkyl ester.

4. The method according to claim 1, wherein the carboxylic acid or its alkyl ester is a $C_{5-6}$ saturated cycloalkane mono- or poly-carboxylic acid which may have a substituent inert to the reaction, or its alkyl ester.

5. The method according to claim 3, wherein the carboxylic acid or its alkyl ester is a $C_{5-24}$ saturated aliphatic monocarboxylic acid or its alkyl ester.

6. The method according to claim 3, wherein the carboxylic acid or its alkyl ester is a $C_{2-24}$ unsaturated aliphatic monocarboxylic acid.

7. The method according to claim 6, wherein the carboxylic acid or its alkyl ester is a $C_{5-24}$ mono-unsaturated aliphatic monocarboxylic acid or its alkyl ester.

8. The method according to claim 1, wherein the carboxylic acid or its alkyl ester is Ar-(COOR)$_n$ wherein n is 1 or 2, R is hydrogen or an alkyl group, and Ar is a phenyl group, a naphthyl group or an anthryl group which may have a group inert to the reaction.

9. The method according to claim 1, wherein the carboxylic acid or its alkyl ester is a carboxylic acid of a 5- or 6-member heterocyclic ring containing at least one N, S or O atom, a carboxylic acid of a condensed ring having at least two such 5- or 6-member heterocyclic rings condensed or a carboxylic acid of a condensed ring having such a 5- or 6-member heterocyclic ring and an aromatic ring condensed, or an alkyl ester thereof.

10. A method for producing an aldehyde, which comprises hydrogenating a carboxylic acid or its alkyl ester with molecular hydrogen in the presence of a catalyst, wherein (1) chromium oxide of high purity having a specific surface area of at least 10 m$^2$/g and a total content of sodium, potassium, magnesium and calcium of not more than 0.4 wt %, is used as a fixed bed catalyst, (2) the carboxylic acid or its alkyl ester is supplied at a concentration of not more than 10 vol % together with molecular hydrogen to the fixed bed catalyst, and (3) the hydrogenation reaction is conducted at a temperature of from 200° to 500° C.

11. The method according to claim 10, wherein the carboxylic acid or its alkyl ester is supplied at a rate (LHSV) of from 0.01 to 2 hr$^{-1}$.

12. The method according to claim 10, wherein the carboxylic acid or its alkyl ester is a $C_{5-24}$ saturated aliphatic monocarboxylic acid or its alkyl ester.

13. The method according to claim 10, wherein the carboxylic acid or its alkyl ester is a $C_{5-24}$ monounsaturated aliphatic monocarboxylic acid or its alkyl ester.

* * * * *